United States Patent
Mandell et al.

(10) Patent No.: US 11,542,550 B2
(45) Date of Patent: Jan. 3, 2023

(54) LABELED NUCLEOTIDES

(71) Applicant: Illumina, Inc., San Diego, CA (US)

(72) Inventors: Jeffrey Mandell, Rancho Santa Fe, CA (US); Steven Barnard, Del Mar, CA (US); John Moon, Rancho Santa Fe, CA (US); Maria Candelaria Rogert Bacigalupo, Encintas, CA (US)

(73) Assignee: Illumina, Inc., San Diego, CA (US)

( * ) Notice: Subject to any disclaimer, the term of this patent is extended or adjusted under 35 U.S.C. 154(b) by 450 days.

(21) Appl. No.: 16/626,425

(22) PCT Filed: Feb. 13, 2019

(86) PCT No.: PCT/US2019/017830
§ 371 (c)(1),
(2) Date: Dec. 24, 2019

(87) PCT Pub. No.: WO2019/160937
PCT Pub. Date: Aug. 22, 2019

(65) Prior Publication Data
US 2020/0157618 A1 May 21, 2020

Related U.S. Application Data

(60) Provisional application No. 62/710,465, filed on Feb. 16, 2018.

(51) Int. Cl.
*C12Q 1/68* (2018.01)
*C07H 19/06* (2006.01)
*C12Q 1/6869* (2018.01)
*B01L 3/00* (2006.01)

(52) U.S. Cl.
CPC ............ *C12Q 1/6869* (2013.01); *B01L 3/502* (2013.01); *C07H 19/06* (2013.01); *B01L 2300/0663* (2013.01); *B01L 2300/12* (2013.01)

(58) Field of Classification Search
CPC ....... C12Q 1/6869; C07H 19/06; B01L 3/502; B01L 2300/0663
See application file for complete search history.

(56) References Cited

U.S. PATENT DOCUMENTS

| | | |
|---|---|---|
| 6,211,356 B1 | 4/2001 | Wiessler et al. |
| 9,151,751 B2 | 10/2015 | Oldham et al. |
| 2002/0039738 A1 | 4/2002 | Williams et al. |

(Continued)

FOREIGN PATENT DOCUMENTS

| | | |
|---|---|---|
| JP | 2017521082 A | 8/2017 |
| RU | 2637310 C1 | 12/2017 |

(Continued)

OTHER PUBLICATIONS

Stratagene Catalog p. 39. (Year: 1988).*

(Continued)

*Primary Examiner* — Jezia Riley
(74) *Attorney, Agent, or Firm* — Illumina, Inc.

(57) ABSTRACT

A labeled nucleotide includes a nucleotide, a linking molecule attached to a phosphate group of the nucleotide, and a redox-active charge tag attached to the linking molecule. The redox-active charge tag is to be oxidized or reduced by an electrically conductive channel when maintained in proximity of a sensing zone of the electrically conductive channel.

20 Claims, 4 Drawing Sheets

(56) References Cited

U.S. PATENT DOCUMENTS

| | | |
|---|---|---|
| 2009/0170716 A1 | 7/2009 | Su et al. |
| 2010/0167938 A1 | 7/2010 | Su et al. |
| 2013/0109577 A1 | 5/2013 | Korlach et al. |
| 2016/0017416 A1 | 1/2016 | Boyanov et al. |
| 2020/0040389 A1* | 2/2020 | Astier .................. C12Q 1/6869 |

FOREIGN PATENT DOCUMENTS

| | | |
|---|---|---|
| WO | 03021010 A2 | 3/2003 |
| WO | 2016010975 A2 | 1/2016 |
| WO | 2017024049 A1 | 2/2017 |
| WO | 2017087974 A1 | 5/2017 |

OTHER PUBLICATIONS

Mucic, Robert C. et al., "Synthesis and characterization of DNA with ferrocenyl groups attached to their 5'-termini: electrochemical characterization of a redox-active nucleotide monolayer", Chem. Commun., 1996, 4, 555-557.

Modak, Anil S. et al., "Toward Chemical Ribonucleases. 2. Synthesis and Characterization of Nucleoside-Bipyridine Conjugates. Hydrolytic Cleavage of RNA by Their Copper(II) Complexes", J. Am. Chem. Soc., vol. 113, No. 1, 1991, pp. 283-291.

Choi, Jung Kyu et al., "Highly Sensitive and Selective Spectroscopic Detection of Mercury(II) in Water by Using Pyridylporphyrin-DNA Conjugates", Chem. Eur. J., 2013, 19, 2515-2522.

Marchan, Vicente et al., "Towards a Better Understanding of the Cisplatin Mode of Action", Chem. Eur. J., 2001, 7, No. 4, 808-815.

Belikov, V. G., "Pharmaceutical chemistry", Textbook, $4^{th}$ edition, Part I., General Pharmaceutical Chemistry, Moscow MEDpress-inform, 2007, 13 pages.

"Molecule" and "Nucleotides", from Chemical encyclopedia: in 5 volumes, vol. 3, Chief ed. I.L. Knunyants, 1992, 22 pages.

"Recommendations for Interstate Standartization RMG 29-2013", Interstate Council for Standardization, Metrology and Certification (ISC), 2014, 3 pages.

International Search Report and Written Opinion for International Application No. PCT/US2019/017830 dated May 8, 2019, 10 pages.

Zhu, H., et al. "Novel Molecular Non-Volatile Memory: Application of Redox-Active Molecules", Applied Sciences, 2016, 6, 7, 15 pages.

Duan, X., et al. "Nonvolatile Memory and Programmable Logic from Molecule-Gate Nanowires", Nano Letters, 2002, vol. 2, No. 5, pp. 487-490.

* cited by examiner

LABELED NUCLEOTIDES

CROSS-REFERENCE TO RELATED APPLICATIONS

This application is a national stage entry under 35 U.S.C. § 371 of PCT/US2019/017830, filed Feb. 13, 2019, which itself claims the benefit of U.S. Provisional Application Ser. No. 62/710,465, filed Feb. 16, 2018, the content of each of which is incorporated by reference herein in its entirety.

BACKGROUND

Various protocols in biological or chemical research involve performing a large number of controlled reactions on local support surfaces or within predefined reaction chambers. The designated reactions may then be observed or detected and subsequent analysis may help identify or reveal properties of chemicals involved in the reaction. In some examples, the controlled reactions generate fluorescence, and thus an optical system may be used for detection. In other examples, the controlled reactions alter charge, conductivity, or some other electrical property, and thus an electronic system may be used for detection.

SUMMARY

A first aspect disclosed herein is a labeled nucleotide. Numbers 1-6 relate to this first aspect.

1. In an example, the labeled nucleotide comprises a nucleotide; a linking molecule attached to a phosphate group of the nucleotide; and a redox-active charge tag attached to the linking molecule, the redox-active charge tag to be oxidized or reduced by an electrically conductive channel when maintained in proximity of a sensing zone of the electrically conductive channel.

2. In the example (1) of the labeled nucleotide, the redox-active charge tag includes a coordinated metal atom that is to undergo a redox reaction.

3. In the example (1) or (2) of the labeled nucleotide, the linking molecule comprises a specificity region attached to the redox-active charge tag.

4. In the example (3), the specificity region is to interact with an acceptor region on a tether bound to the electrically conductive channel, and the specificity region includes an affinity tag.

5. In the example (4), the specificity region is to hybridize to the acceptor region on the tether bound to the electrically conductive channel, and the affinity tag includes a nucleotide sequence including from one about nucleotide to about ten nucleotides or a peptide nucleic acid sequence including from about one peptide nucleic acid to about ten peptide nucleic acids.

6. In any of the examples (1) through (5) of the labeled nucleotide, the redox-active charge tag includes 10 charges or fewer in a non-oxidized or non-reduced state; and the redox-active charge tag includes from about 1 charge to about 100 charges in an oxidized or reduced state.

It is to be understood that any features of the labeled nucleotide disclosed herein, including examples (1) through (6), may be combined together in any desirable manner and/or configuration.

A second aspect disclosed herein is a method. Numbers 7-18 relate to this second aspect.

7. In an example, the method comprises introducing a template nucleic acid to an electrically conductive channel having a polymerase tethered thereto; introducing labeled nucleotides to the electrically conductive channel, at least one of the labeled nucleotides including a nucleotide and a nucleotide-specific redox-active charge tag attached thereto, whereby one of the labeled nucleotides associates with the polymerase; while the one of the labeled nucleotides is associated, initiating a redox reaction between the nucleotide-specific redox-active charge tag and the electrically conductive channel to alter a charge state of the nucleotide-specific redox-active charge tag; and in response to the redox reaction, detecting a response of the electrically conductive channel.

8. In the example (7) of the method, initiating the redox reaction involves applying a charging voltage to the electrically conductive channel; and detecting the response of the electrically conductive channel involves applying a reading voltage to the electrically conductive channel.

9. An example of the method (7) or (8) further comprises associating the response of the electrically conductive channel with the nucleotide-specific redox-active charge tag of the associated one of the labeled nucleotides; and based on the nucleotide-specific redox-active charge tag, identifying the nucleotide of the associated labeled nucleotide.

10. The example (9) may also further comprise cleaving the nucleotide-specific redox-active charge tag from the associated one of the labeled nucleotides, whereby the nucleotide of the associated labeled nucleotide is incorporated into a nascent strand complementary to the template nucleic acid.

11. In the example (10), the associating of the one of the labeled nucleotides, the initiating of the redox reaction, the detecting, the associating, and the identifying together are a sequencing cycle; and the method further comprises performing a next sequencing cycle by allowing a next one of the labeled nucleotides to associate with the polymerase; while the next one of the labeled nucleotides is associated, initiating another redox reaction between another nucleotide-specific redox-active charge tag and the electrically conductive channel to alter a charge state of the other nucleotide-specific redox-active charge tag; in response to the other redox reaction, detecting another response of the electrically conductive channel; associating the other response of the electrically conductive channel with the other nucleotide-specific redox-active charge tag; and based on the other nucleotide-specific redox-active charge tag, identifying the nucleotide of the next one of the labeled nucleotides.

12. The example (11) may also further comprise cleaving the other nucleotide-specific redox-active charge tag of the next one of the labeled nucleotides, whereby the nucleotide of the next one of the labeled nucleotides is incorporated into the nascent strand complementary to the template nucleic acid; and repeating the sequencing cycle.

13. In any of examples (7) through (12) of the method, the redox-active charge tag includes a coordinated metal atom that is to undergo a redox reaction.

14. In any of examples (7) through (13) of the method, the redox-active charge tag includes 10 charges or fewer in a non-oxidized or non-reduced state; and the redox-active charge tag includes from about 1 charge to about 100 charges in an altered charge state.

15. In any of examples (7) through (14) of the method, the labeled nucleotides include a first labeled nucleotide including deoxyadenosine polyphosphate as the nucleotide and a first nucleotide-specific redox-active charge tag; a second labeled nucleotide including deoxyguanosine polyphosphate as the nucleotide and a second nucleotide-specific redox-active charge tag; a third labeled nucleotide including deoxycytidine polyphosphate as the nucleotide and a third nucleotide-specific redox-active charge tag; and a fourth labeled nucleotide including deoxythymidine polyphosphate as the nucleotide and a fourth nucleotide-specific redox-active charge tag; and the first, second, third, and fourth nucleotide-specific redox-active charge tags are different from each other.

16. In the example (15), two of the first, second, third, and fourth nucleotide-specific redox-active charge tags are positively charged in an altered charge state, and wherein another two of the first, second, third, and fourth nucleotide-specific redox-active charge tags are negatively charged in the altered charge state.

17. In any of examples (7) through (16) of the method, the labeled nucleotides are present in a low salt buffer.

18. In any of examples (7) through (17) of the method, the electrically conductive channel is a channel of a field effect transistor.

It is to be understood that any features of the method, including examples (7) through (17), may be combined together in any desirable manner. Moreover, it is to be understood that any combination of features of this method and/or of the labeled nucleotide may be used together, and/or combined with any of the examples disclosed herein.

A third aspect disclosed herein is a kit. Numbers 19-22 relate to this third aspect.

19. In an example, the kit comprises a flow cell, including an electrically conductive channel having a tether attached thereto and a polymerase attached to the electrically conductive channel via the tether; a template nucleic acid to be introduced into the flow cell; reagents to be introduced into the flow cell, the reagents including labeled nucleotides, at least one of the labeled nucleotides including: a nucleotide; a linking molecule attached to a phosphate group of the nucleotide; and a redox-active charge tag attached to the linking molecule, the redox-active charge tag to be oxidized or reduced by the electrically conductive channel when maintained in proximity of a sensing zone of the electrically conductive channel; and a detector to detect a response from the electrically conductive channel when a redox reaction takes place between the redox-active charge tag and the electrically conductive channel.

20. In the example (19) of the kit, the redox-active charge tag is selected from the group consisting of ferrocene, zinc tetrabenzoporphyrin, cobalt phthalocyanine, tris-(2,2'-bipyrimidine)ruthenium, 4-ferrocenylbenzyl alcohol, 5-(4-hydroxymethylphenyl)-10,15,20-trimesitylporphinatozinc(II), and a redox-active calixarene.

21. In any of examples (19) or (20) of the kit, the redox-active charge tag includes 10 charges or fewer in a non-oxidized or non-reduced state; and the redox-active charge tag includes from about 1 charge to about 100 charges in an oxidized or reduced state.

22. In any of examples (19) through (21) of the kit, the electrically conductive channel is a channel of a field effect transistor.

It is to be understood that any features of this kit, including examples (19) through (22), may be combined together in any desirable manner. Moreover, it is to be understood that any combination of features of this kit and/or of the method and/or of the labeled nucleotide may be used together, and/or combined with any of the examples disclosed herein.

Still further, it is to be understood that any features of any of the labeled nucleotides and/or of any of the methods and/or of any of the kits may be combined together in any desirable manner, and/or may be combined with any of the examples disclosed herein.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

Labeled nucleotides are disclosed herein which may be used for single molecule detection in nucleic acid sequencing procedures. A sensor used in single molecule detection may have one electrically conductive channel with one polymerase attached thereto. This enables one incorporation event (i.e., the incorporation of a base into a nascent strand by the polymerase) to be detected at a time at each individual sensor. The labeled nucleotides provide a unique detection modality that can be used for nucleic acid sequencing and for detection of nucleic acids and other analytes in general.

Figure 1:
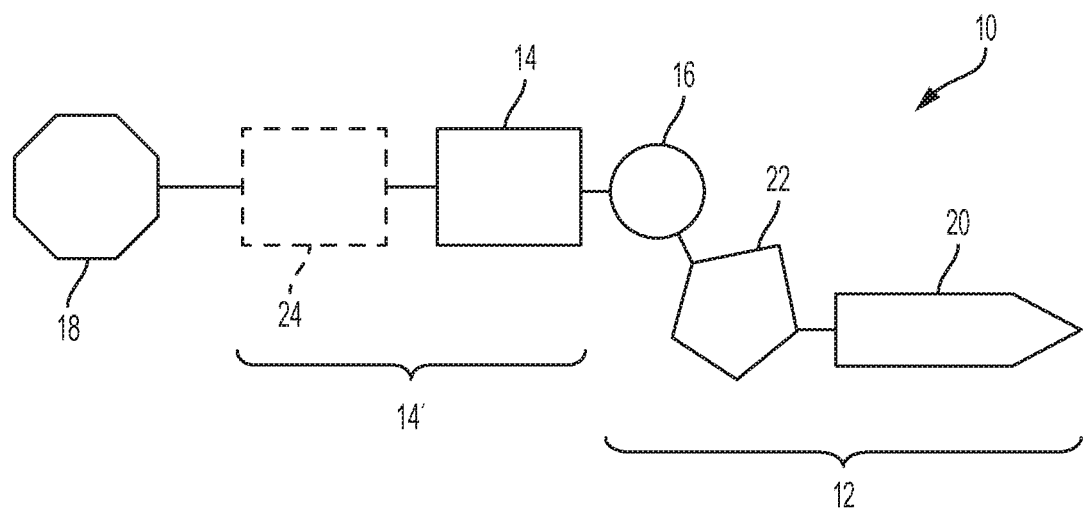
FIG. 1 is a schematic illustration of an example of a labeled nucleotide.

An example of the labeled nucleotide 10 is schematically depicted in FIG. 1. As shown, the labeled nucleotide 10 includes a nucleotide 12, a linking molecule 14 or 14' attached to a phosphate group 16 of the nucleotide 12, and a redox-active charge tag 18 attached to the linking molecule 14 or 14', the redox-active charge tag 18 to be oxidized or reduced by an electrically conductive channel (reference numeral 32, FIG. 2) when maintained in proximity of a sensing zone (reference numeral 31, FIG. 3) of the electrically conductive channel 32. The labeled nucleotide 10 may be considered a non-natural or synthetic nucleotide because it is structurally or chemically distinct from a natural nucleotide.

The nucleotide 12 of the labeled nucleotide 10 may be a natural nucleotide. Natural nucleotides include a nitrogen-containing heterocyclic base 20, a sugar 22, and one or more phosphate groups 16. Examples of natural nucleotides include, for example, ribonucleotides or deoxyribonucleotides. In a ribonucleotide, the sugar 22 is a ribose, and in deoxyribonucleotides, the sugar 22 is a deoxyribose, i.e. a sugar lacking a hydroxyl group that is present at the 2' position in ribose. In an example, the nucleotide 12 is in the polyphosphate form because it includes several phosphate groups 16 (e.g., tri-phosphate (i.e., gamma phosphate), tetra-phosphate, penta-phosphate, hexa-phosphate, etc.).

The heterocyclic base 20 (i.e., nucleobase) can be a purine base or a pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine. A nucleic acid analog may have any of the phosphate backbone, the sugar, or the nucleobase altered. Examples of nucleic acid analogs include, for example, universal bases or phosphate-sugar backbone analogs, such as peptide nucleic acids (PNA).

The labeled nucleotide 10 also includes the linking molecule 14 or 14'. In some examples, the linking molecule (shown as 14 in FIG. 1) does not include a specificity region 24. In other examples, the linking molecule (shown as 14' in FIG. 1) does include the specificity region 24. As is schematically depicted in FIG. 1, when the specificity region 24 is part of the linking molecule 14', the region 24 may be located at the end that chemically bonds to the redox-active charge tag 18. The specificity region 24 will be described further hereinbelow.

Figure 2:
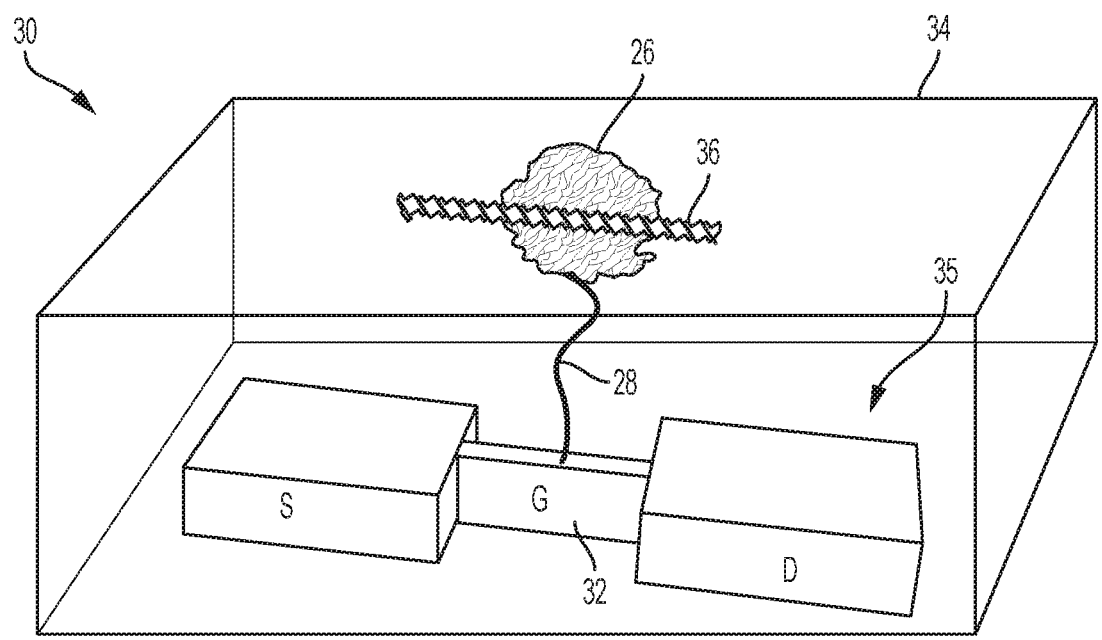
FIG. 2 is a schematic and partially perspective view of an example of a system disclosed herein.

The linking molecule 14 or 14' of the labeled nucleotide 10 may be any long chain molecule that can chemically bond, at one end, to the phosphate group 16 of the nucleotide 12 and that can chemically bond, at the other end, to the redox-active charge tag 18. The linking molecule 14 or 14' may also be selected so that it will not interact with a polymerase 26 used in the system 30 (see FIG. 2) disclosed herein. The linking molecule 14 or 14' is selected so that it is long enough to permit the redox-active charge tag 18 to reside within the sensing zone 31 (FIG. 3) of the electrically conductive channel 32 (FIG. 2). As examples, the linking molecule 14 or 14' may include an alkyl chain, a poly(ethylene glycol) chain, an amido group, a phosphate group, a heterocycle such as a triazole, nucleotides, or combinations thereof. Examples of the alkyl chain may include at least 6 carbon atoms and examples of the poly(ethylene glycol) chain may include at least 3 ethylene glycol units.

The following example illustrates an example of the labeled nucleotide 10, where the linking molecule 14, 14' comprises an alkyl chain, an amide group, a poly(ethylene glycol) chain, and a triazole:

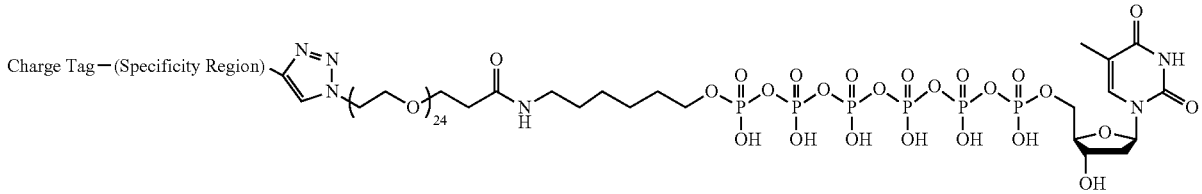

The following example illustrates another example of the labeled nucleotide 10, where the linking molecule 14, 14' comprises alkyl chains, an amide group, poly(ethylene glycol) chains, a triazole, and a phosphate group:

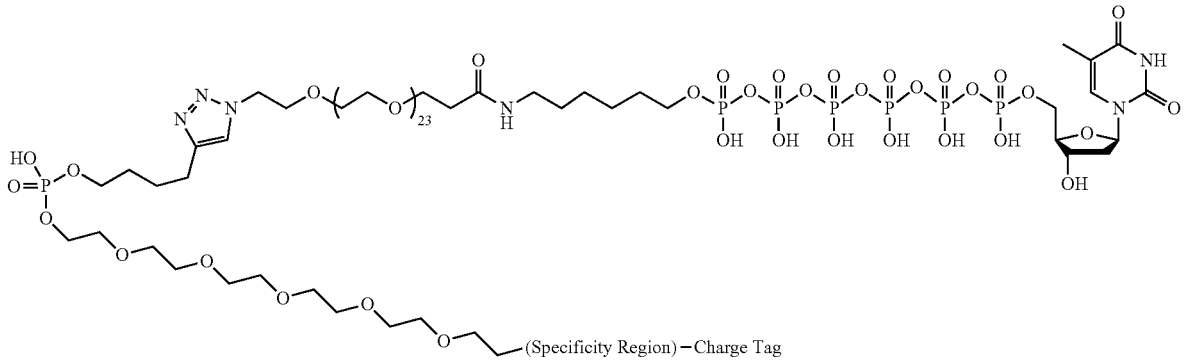

The following example illustrates yet another example of the labeled nucleotide 10, where the linking molecule 14, 14' comprises alkyl chains, amide groups, poly(ethylene glycol) chains, a triazole, and a phosphate group:

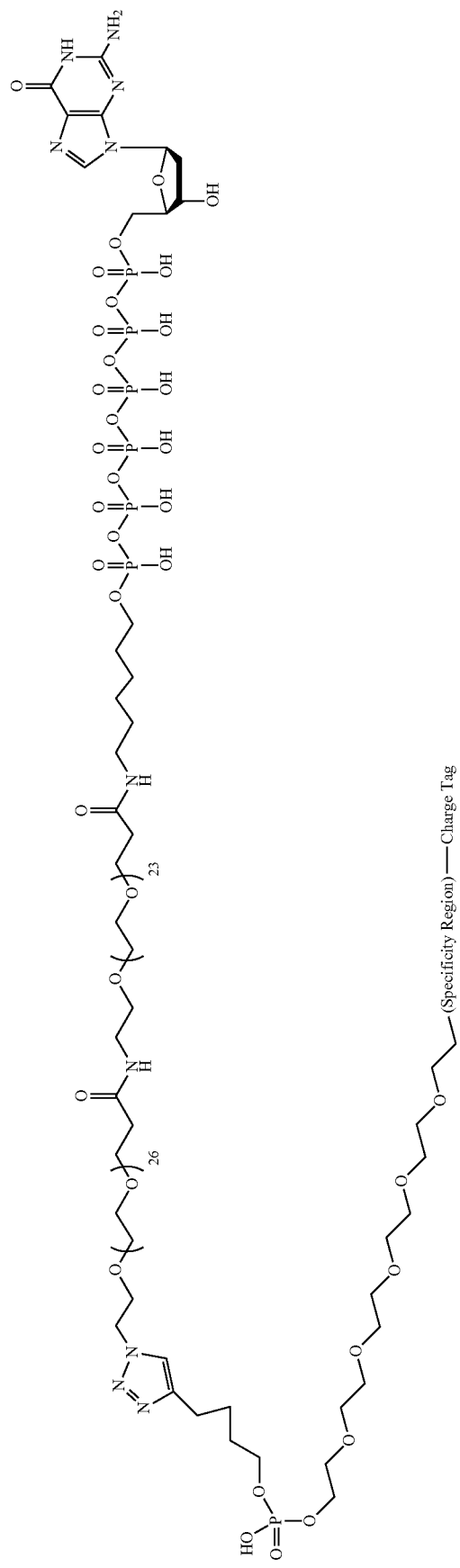

The following example illustrates still a further example of the labeled nucleotide 10, where the linking molecule 14, 14' comprises an alkyl chains, an amide group, poly(ethylene glycol) chains, a triazole, a phosphate group and a polynucleotide chain:

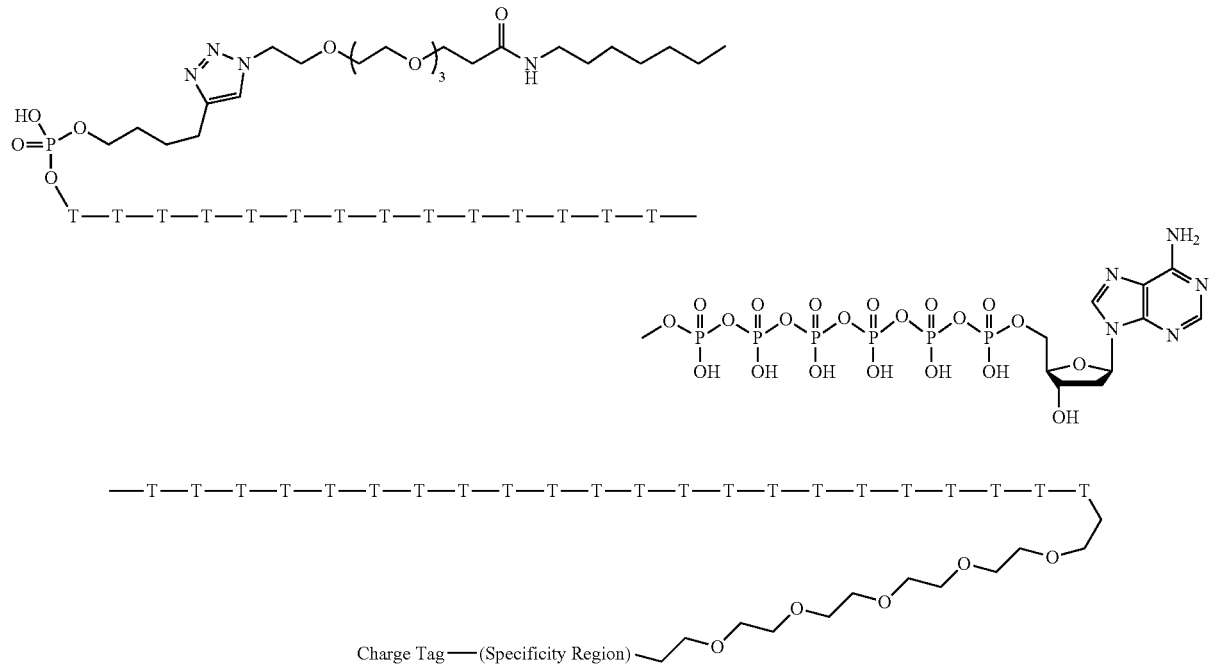

While several example linking molecules 14, 14' have been described, it is to be understood that other linking molecules 14, 14' may be used.

As shown in FIG. 1 and the previous examples, some of the labeled nucleotides 10 may also include the specificity region 24 as part of the linking molecule 14'. The specificity region 24 is capable of interacting with an acceptor region on a tether 28 (FIG. 2) that is bound to the electrically conductive channel 32. The specificity region 24 may include an affinity tag, which can temporarily attach to the acceptor region of the tether 28. The binding affinity of the affinity tag may be strong enough to bind the specificity region 24 to the acceptor region on the tether 28 when the labeled nucleotide 10 is held by the polymerase 26, but may also be weak enough to release the specificity region 24 from the acceptor region after an incorporation event (e.g., when the polymerase 26 naturally cleaves the bond between the alpha phosphate and the linking molecule 14, 14' or between the alpha phosphate and beta phosphate). In other words, the on- and off-rates of the specificity region 24 (e.g., affinity tag) to and from the acceptor region may be selected to improve overall single molecule sensing. The on-rate of the affinity tag/acceptor region interaction may be high, for example, due to an effectively high concentration of the specificity region 24, and thus the affinity tag, before nucleotide incorporation. This high on-rate increases the fraction of time that the affinity tag is bound to the acceptor region. After cleavage, the off-rate of the interaction may also be selected to be high enough that the complex (between the affinity tag and the acceptor region) dissociates rapidly enough that there is a low probability of a bound state (between the affinity tag of the previously incorporated nucleotide and the acceptor region) when the next labeled nucleotide 10 enters the polymerase 26 active site.

In a specific example, the specificity region 24 is to hybridize to the acceptor region on the tether 28, and so the affinity tag may include a nucleotide sequence or a peptide nucleic acid sequence that is capable of temporarily attaching to the acceptor region on the tether 28 (FIG. 2). In an example, the affinity tag includes a nucleotide sequence including from about one nucleotide to about ten nucleotides or from about one peptide nucleic acid to about ten peptide nucleic acids. In other examples, the affinity tag includes up to six nucleotides or peptide nucleic acids. In still another example (as shown and described further in FIG. 5B), the specificity region 24 may further include inosine(s) flanking both sides of the nucleotide sequence. In yet other examples, the affinity tag may be a non-nucleic acid moiety, such as peptides that have affinity to each other or to hydrophobic polymers. A specific protein example includes a coiled coil, which is a structural motif in proteins in which 2-7 alpha-helices are coiled together like the strands of a rope. In other words, coiled coils are built by two or more alpha-helices that wind around each other to form a supercoil. Examples of coiled coils include oncoproteins like c-Fos and c-jun.

The redox-active charge tag 18 may be any charge tag that is capable of increasing its charge when oxidized (losing an electron) or reduced (gaining an electron) by the electrically conductive channel 32, for example, when maintained in proximity of a sensing zone 31 of the electrically conductive channel 32. The charge tag 18 may be net neutral (zero charge), or close to this state (10 charges or fewer), before the redox reaction takes place. In other words, in the non-oxidized or non-reduced state, the redox-active charge tag 18 carries 10 charges or fewer. The charges carried by the redox-active charge tag 18 do not include any charge of the phosphate 16 or of the linking molecule 14, 14' of the labeled nucleotide 10. After the redox reaction takes place, the net overall charge of the redox-active charge tag 18 changes (i.e., it carries more positive charges or more negative charges). In an example, the redox-active charge tag 18 includes 10 charges or fewer in a non-oxidized or non-reduced state, and the redox-active charge tag 18 includes from about 1 charge to about 100 charges in an oxidized or reduced state. It is to be understood that the number of charges of the redox-active charge tag 18 in the non-oxidized or non-reduced state is lower than the number of charges of the redox-active charge tag 18 in the oxidized or reduced state. In another example, the redox-active charge tag 18 includes 10 charges or fewer in a non-oxidized or non-reduced state, and the redox-active charge tag 18 includes from about 20 charges to about 50 charges in an oxidized or reduced state.

The redox-active charge tag 18 may include any coordinated (i.e., held in place) metal atom that can undergo a redox reaction. Examples of the metal atoms include iron, cobalt, ruthenium, zinc, copper, lithium, silver, etc. As some specific examples, the redox-active charge tag 18 is selected from the group consisting of ferrocene, zinc tetrabenzoporphyrin, cobalt phthalocyanine, tris-(2,2'-bipyrimidine)ruthenium, 4-ferrocenylbenzyl alcohol, 5-(4-hydroxymethylphenyl)-10,15,20-trimesitylporphinatozinc(II), and a redox-active calixarene.

Ferrocene may be any organometallic compound that includes the formula $Fe(C_5H_5)_2$. A specific example is the ferrocene dendrimer:

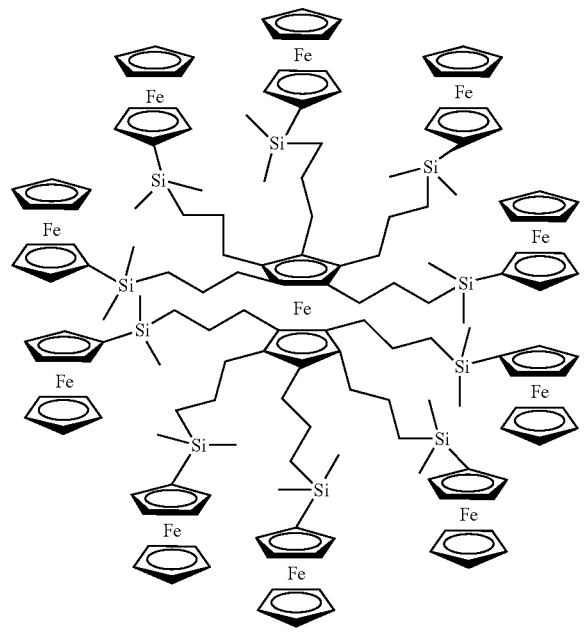

in which $Fe^{2+}$ can become $Fe^{3+}$ upon oxidation, thus introducing a positive charge at each "Fe".

Zinc tetrabenzoporphyrin has the structure:

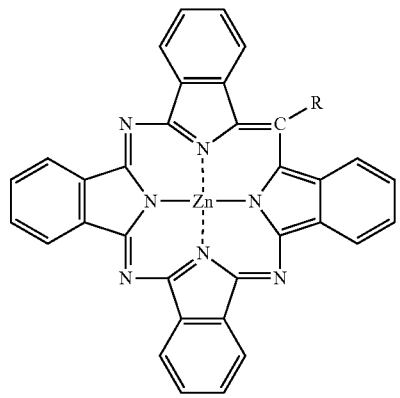

where $R=C_2H_5$, $C_6H_{13}$, or $C_{12}H_{25}$. The $Zn^{1+}$ can become $Zn^{2+}$ upon oxidation, thus introducing a positive charge.

Examples of cobalt phthalocyanine include:

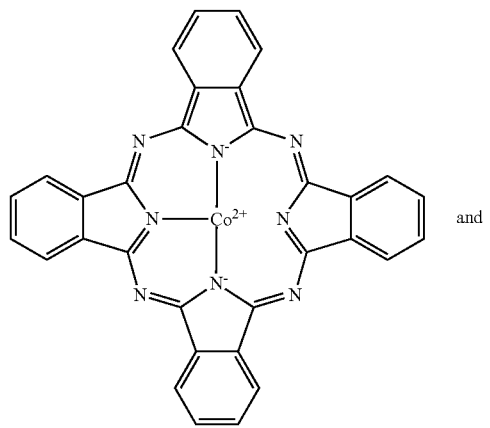

and

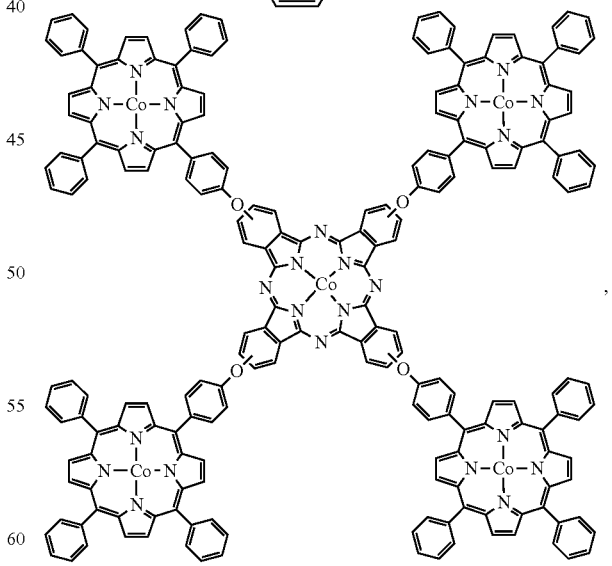

both of which are net-neutral molecules in solution. Upon oxidation, the $Co^{2+}$ becomes $Co^{3+}$, thus introducing a positive charge at each "Co" (e.g., one positive charge for the first structure and five positive charges for the second structure). Other cobalt containing compounds with oxidation states ranging from −3 to +5 are known and may be used as negatively chargeable redox-active charge tags 18 or positively chargeable redox-active charge tags 18.

Tris-(2,2'-bipyrimidine)ruthenium has the structure:

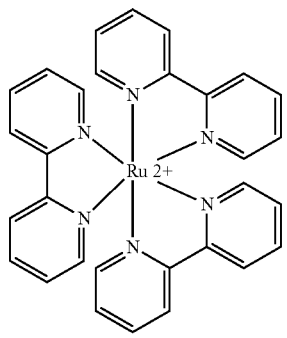

in which $Ru^2+$ can become $Ru^3+$ upon oxidation, thus introducing a positive charge.

4-ferrocenylbenzyl alcohol has the structure:

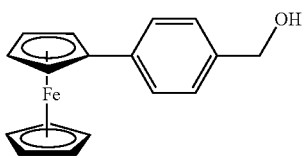

in which $Fe^2+$ can become $Fe^3+$ upon oxidation, thus introducing a positive charge.

5-(4-hydroxymethylphenyl)-10,15,20-trimesitylporphinatozinc(II) has the structure:

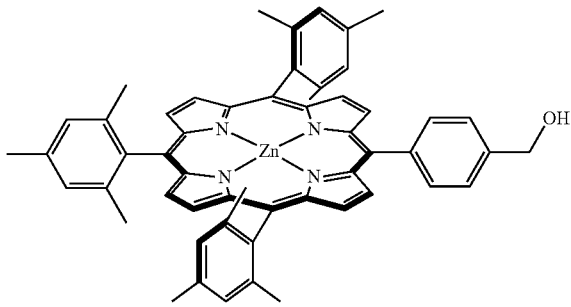

in which $Zn^2+$ can become $Zn^1+$ upon reduction, thus introducing a negative charge.

Some examples of redox-active calixarenes include:

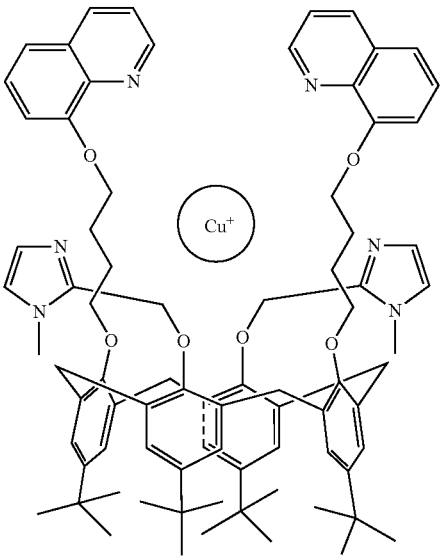

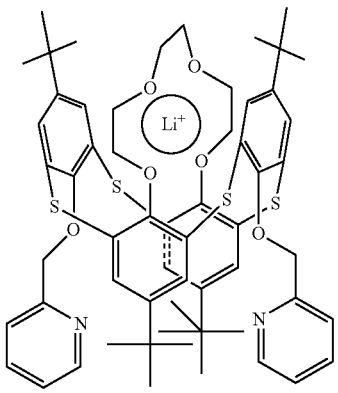

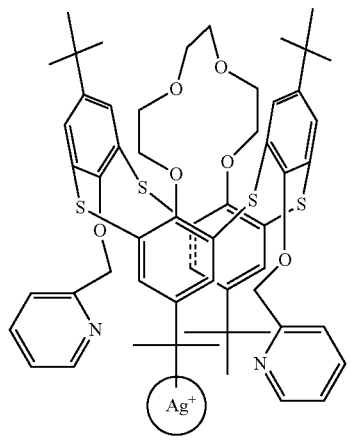

-continued

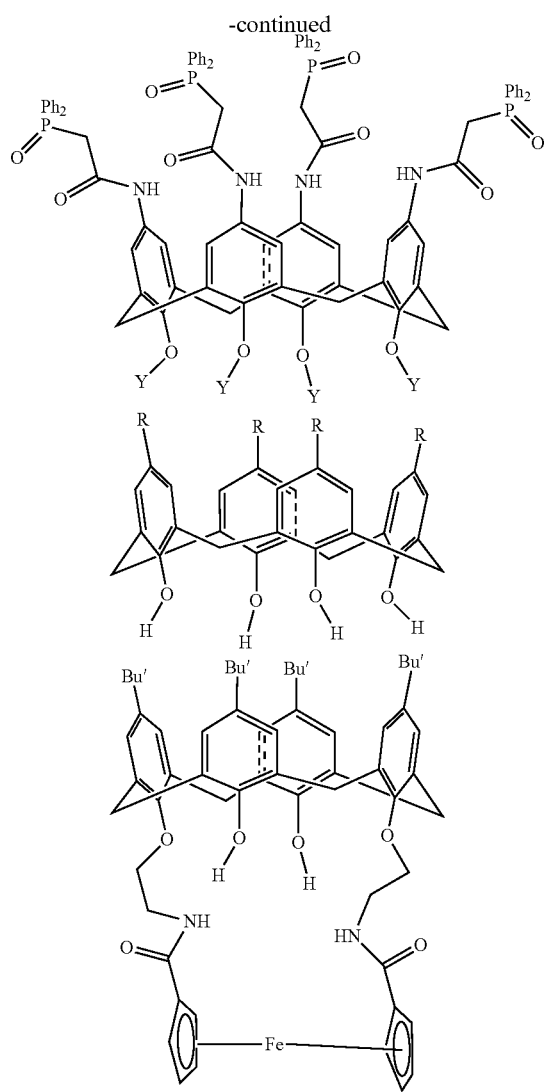

Each of the previously described redox reactions is reversible, and thus the compounds may be used in their higher oxidation state and may be reduced when in the electrically conductive channel sensing zone 31, or may be used in their lower oxidation state and may be oxidized when in the electrically conductive channel sensing zone 31.

As mentioned above, the redox-active charge tag 18 disclosed herein may be neutral or near-neutral in solution, and does not carry a larger charge until it undergoes a redox reaction. As such, the labeled nucleotides 10 in solution are not considered highly charged molecules, and agglomeration among oppositely charged labeled nucleotides 10 (containing oppositely charged near-neutral redox-active charge tags 18) is less likely to occur.

The labeled nucleotides 10 may be used in kit and/or in a system 30 (an example of the latter of which is shown in FIG. 2). The kit or system 30 may include the electrically conductive channel 32. The electrically conductive channel 32 may be within or part of a vessel, such as a well, tube, channel, cuvette, Petri plate, bottle, or the like. Another example of a suitable vessel is a flow cell 34. Any flow cell configuration suitable for the implementations described herein may be used. Some example flow cells are those that are commercially available from Illumina, Inc. (San Diego, Calif.). Flow cells 34 are convenient for delivering bulk reagents to an array of individually addressable electrically conductive channels 32 during attachment of reaction components (e.g., template nucleic acids, labeled nucleotides 10, etc.) to the respective electrically conductive channels 32 or during subsequent reactions carried out with the reaction components on respective electrically conductive channels 32. Cyclic processes, such as nucleic acid sequencing reactions, are particularly well suited for flow cells 34. Another particularly useful vessel is a well in a multiwell plate or microtiter plate.

In the example shown in FIG. 2, the flow cell 34 includes the electrically conductive channel 32. As used herein, the term "electrically conductive channel" is intended to mean a portion of a detection device that translates perturbations at its surface or in its surrounding electrical field into an electrical signal. For example, a electrically conductive channel 32 can translate the arrival or departure of a reaction component (e.g., the labeled nucleotide 10) into an electrical signal. In the examples disclosed herein, the electrically conductive channel 32 can also translate interactions between two reaction components (the template nucleic acid and a nucleotide 20 of the labeled nucleotide 10) into a detectable signal through its interaction with the redox-active charge tag 18 of the labeled nucleotide 10.

The electrically conductive channel 32 may be the channel of a charge sensor 35. The charge sensor 35 may include source and drain terminals S, D and the channel 32 connecting the terminals S, D. The channel 32 may have any suitable geometry, such as, for example, a tube, a wire, a plate, etc.

The terminals S, D may be any suitable conductive material. Examples of suitable source and drain materials include cobalt, cobalt silicide, nickel, nickel silicide, aluminum, tungsten, copper, titanium, molybdenum, indium tin oxide (ITO), indium zin oxide, gold, platinum, carbon, etc.

The electrically conductive channel 32 may include any conductive or semi-conductive material that can oxidize or reduce the redox-active charge tag 18. The material may comprise an organic material, an inorganic material, or both. Some examples of suitable channel materials include silicon, carbon (e.g., glassy carbon, graphene, etc.), polymers, such as conductive polymers (e.g., polypyrrole, polyaniline, polythiophene, poly(3,4-ethylenedioxythiophene) doped with poly(4-styrenesulfonate) (PEDOT-PSS), etc.), metals, etc.

In some examples, the electrically conductive channel 26 may also be a nanostructure that has at least one dimension on the nanoscale (ranging from 1 nm to less than 1 µm). In one example, this dimension refers to the largest dimension. As examples, the electrically conductive channel 26 may be a semi-conducting nanostructure, a graphene nanostructure, a metallic nanostructure, and a conducting polymer nanostructure. The nanostructure may be a multi- or single-walled nanotube, a nanowire, a nanoribbon, etc.

An example charge sensor 35 is a field effect transistor (FET), such as a carbon nanotube (CNT) based FET, single-walled carbon nanotube (SWNT) based FET, silicon nanowire (SiNW) FET, a polymer nanowire FET, a graphene nanoribbon FET (and related nanoribbon FETs fabricated from 2D materials such as $MoS_2$, silicene, etc.), tunnel FET (TFET), and steep subthreshold slope devices.

The example charge sensor 35 shown in FIG. 2 is a nanostructure FET including the source S, the drain D, and the electrically conductive channel 32 between the source S and the drain D. The electrically conductive channel 32 may be a carbon nanotube, a single-walled carbon nanotube, a silicon nanowire, a polymer nanowire, etc. The electrically conductive channel 32 functions as the gate terminal, and thus is also shown as "G" in FIG. 2. In the examples disclosed herein, the gate G/electrically conductive channel 32 may serve as a redox electrode (providing or accepting electrons) for the redox-active charge tag 18 of the labeled nucleotide 10. More specifically, the gate G/electrically conductive channel 32 may be used to transfer electrons to or from the redox-active charge tag 18. Electron transfer may occur via tunneling through a gate oxide (not shown) on at least a portion of the surface of the gate G/electrically conductive channel 32. In some examples, the thickness of the gate oxide may be used to modulate current transfer efficiency such that a minimum amount of contact time passes before the redox-active charge tag 18 becomes sufficiently activated. Contact time may refer to the time that redox-active charge tag 18 is held within sufficient proximity of the gate G/electrically conductive channel 32 for electron transfer to occur with a high likelihood. This time period will depend on many factors, including the type of redox-active charge tag 18, the gate oxide thickness, and the distance of the charge tag 18 from the gate G/electrically conductive channel 32. This may be used to ensure that the charge sensor 35 sufficiently differentiates between diffusing labeled nucleotides 10 that transiently contact the gate G/electrically conductive channel 32 but that are not actually associated with the polymerase 26 attached to the gate G/electrically conductive channel 32. Nucleotides 10 that are associated with the active site of the polymerase 26 are expected to remain in the associated state for a time period that is significantly longer than the time that a transient interaction occurs. For instance, the labeled nucleotide 10 may remain associated with the polymerase active site (e.g., polymerase 26) for hundreds of microseconds to hundreds of milliseconds. A transient interaction would occur on diffusion timescales which are orders of magnitude faster.

In this example, the polymerase 26 is immobilized on the gate G/electrically conductive channel 32 of the charge sensor 32 with a tether 28. The tether 28 is used as an anchor for the polymerase 26. The tether 28 may exhibit electron transport capability. Examples of suitable tethers 28 include nucleic acid chains (e.g., having 5 to 25 nucleotides), peptides, single carbon chains, non-conductive or low conductive oligomers or polymers, etc.

In some examples, the tether 28 holds the polymerase 26 at least 10 nm away from the gate G/electrically conductive channel 32 of the charge sensor 35. This may be desirable, for example, when it is not desirable to sense the charges of the polymerase 26 and/or the negative charges of the template nucleic acid 36 held by the polymerase 26. However, if it is desirable to sense the polymerase 26 and/or template nucleic acid 36 charges, then the tether 28 may hold the polymerase 26 less than about 10 nm, less than about 9 nm, less than about 8 nm, less than about 7 nm, less than about 6 nm, less than about 5 nm, less than about 4 nm, less than about 3 nm, less than about 2 nm, or about 1 nm from the gate G of the charge sensor 32.

The use of the FET-based charge sensor 35 may enable the following: (1) single-molecule sensitivity can be achieved with a properly designed FET, and (2) high degree of parallelization (also called "multiplexability") can be facilitated since the detected change in charge is localized in the vicinity of the gate G/electrically conductive channel 32, thereby avoiding cross-talk between neighboring, individually addressable FET sites (e.g., in an array). Moreover, silicon nanostructure FET can be manufactured using processes that are compatible with semiconductor manufacturing facilities.

Examples of the kit and/or system 30 may also include a template nucleic acid 36 that is to be introduced into the flow cell 34 and reagents (not shown in FIG. 2) that are to be introduced into the flow cell 34.

The template nucleic acid 36 may be any sample that is to be sequenced, and may be composed of DNA, RNA, or analogs thereof. The source of the template (or target) nucleic acids 36 can be genomic DNA, messenger RNA, or other nucleic acids from native sources. In some cases, the template nucleic acids 36 that are derived from such sources can be amplified prior to use in a method or system 30 herein. Any of a variety of known amplification techniques can be used including, but not limited to, polymerase chain reaction (PCR), rolling circle amplification (RCA), multiple displacement amplification (MDA), or random primer amplification (RPA). It is to be understood that amplification of target nucleic acids 26 prior to use in the method or system 30 set forth herein is optional. As such, template nucleic acids 36 will not be amplified prior to use in some examples. Template/target nucleic acids can optionally be derived from synthetic libraries. Synthetic nucleic acids can have native DNA or RNA compositions or can be analogs thereof.

Biological samples from which template nucleic acids 36 can be derived include, for example, those from a mammal, such as a rodent, mouse, rat, rabbit, guinea pig, ungulate, horse, sheep, pig, goat, cow, cat, dog, primate, human or non-human primate; a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a *Dictyostelium discoideum*; a fungi such as *Pneumocystis carinii Takifugu rubripes*, yeast, *Saccharamoyces cerevisiae* or *Schizosaccharomyces pombe*; or a *Plasmodium falciparum*. Template nucleic acids 36 can also be derived from prokaryotes such as a bacterium, *Escherichia coli*, staphylococci or *Mycoplasma pneumoniae*; an archae; a virus such as Hepatitis C virus, ebola virus or human immunodeficiency virus; or a viroid. Template nucleic acids 36 can be derived from a homogeneous culture or population of the above organisms or alternatively from a collection of several different organisms, for example, in a community or ecosystem.

Moreover, template/target nucleic acids 36 may not be derived from natural sources, but rather can be synthesized using known techniques. For example, gene expression probes or genotyping probes can be synthesized and used in the examples set forth herein.

In some examples, template/target nucleic acids 36 can be obtained as fragments of one or more larger nucleic acids. Fragmentation can be carried out using any of a variety of techniques known in the art including, for example, nebulization, sonication, chemical cleavage, enzymatic cleavage, or physical shearing.

Fragmentation may also result from use of a particular amplification technique that produces amplicons by copying only a portion of a larger nucleic acid. For example, PCR amplification produces fragments having a size defined by the length of the nucleotide sequence on the original template that is between the locations where flanking primers hybridize during amplification.

A population of template/target nucleic acids 36, or amplicons thereof, can have an average strand length that is desired or appropriate for a particular application of the methods, kits, or system 30 set forth herein. For example, the average strand length can be less than about 100,000 nucleotides, 50,000 nucleotides, 10,000 nucleotides, 5,000 nucleotides, 1,000 nucleotides, 500 nucleotides, 100 nucleotides, or 50 nucleotides. Alternatively or additionally, the average strand length can be greater than about 10 nucleotides, 50 nucleotides, 100 nucleotides, 500 nucleotides, 1,000 nucleotides, 5,000 nucleotides, 10,000 nucleotides, 50,000 nucleotides, or 100,000 nucleotides. The average strand length for a population of target nucleic acids, or amplicons thereof, can be in a range between a maximum and minimum value set forth above.

In some cases, a population of template/target nucleic acids 36 can be produced under conditions or otherwise configured to have a maximum length for its members. For example, the maximum length for the members can be less than about 100,000 nucleotides, 50,000 nucleotides, 10,000 nucleotides, 5,000 nucleotides, 1,000 nucleotides, 500 nucleotides, 100 nucleotides or 50 nucleotides. Alternatively or additionally, a population of template nucleic acids 36, or amplicons thereof, can be produced under conditions or otherwise configured to have a minimum length for its members. For example, the minimum length for the members can be more than about 10 nucleotides, 50 nucleotides, 100 nucleotides, 500 nucleotides, 1,000 nucleotides, 5,000 nucleotides, 10,000 nucleotides, 50,000 nucleotides, or 100,000 nucleotides. The maximum and minimum strand length for template nucleic acids 36 in a population can be in a range between a maximum and minimum value set forth above.

As shown in FIG. 2, the template nucleic acid 36 (e.g., a single stranded DNA strand) to be sequenced is bound to the polymerase 26 after having been introduced in a fluid along with or separate from reagents, such as the previously described labeled nucleotides 10 (not shown in FIG. 2).

The template nucleic acid 36 and/or the reagents (e.g., labeled nucleotides 10) may be present in a fluid and introduced into the flow cell 34. The fluid may include a low salt buffer. As examples, the low salt buffer may include from greater than 0 mM to about 50 mM salt. As one example, the low salt buffer may include up to 5 mM $Mg^{2+}$ in Tris buffer (pH 8.0). The use of a low salt buffer may be desirable so that the sensing zone 31 (i.e., Debye length) is not adversely affected, i.e., is not too long so as to preclude sensing of the charge tags 18. The fluid may also include catalysts, such as enzymes, that facilitate a reaction, other additives, and solvents (e.g., water, dimethyl sulfoxide (DMSO), betaine, formamide, etc.).

In some examples, several different labeled nucleotides 10 may be used together in the fluid that is introduced to the charge sensor 35. In these examples, it is to be understood that the linking molecule 14, 14' could be either identical for all labeled nucleotide types, or could be different. Properties of the linking molecule 14, 14', such as length and rigidity, can be altered so as to affect the rate of the redox reaction. Such properties can be tuned individually for a labeled nucleotide 10 and its associated redox-active charge tag 18. Properties of the specificity region 24 of the linking molecule 14' can also be altered to affect the rate of the redox reaction. The linking molecule 14, 14' can be altered to increase or decrease the amount of time the redox-active charge tag 18 is in proximity to the electrically conductive channel 32. Such alterations can be used to affect the rate of electron transfer. In so doing, transient interactions between the charge tag 18 and the electrically conductive channel 32 from diffusing labeled nucleotides 10 can be made less likely to result in electron transfer. Alternatively, holding the redox-active charge tag 18 for a longer period in close proximity to the electrically conductive channel 32 can result in a higher likelihood of electron transfer.

Figure 3:
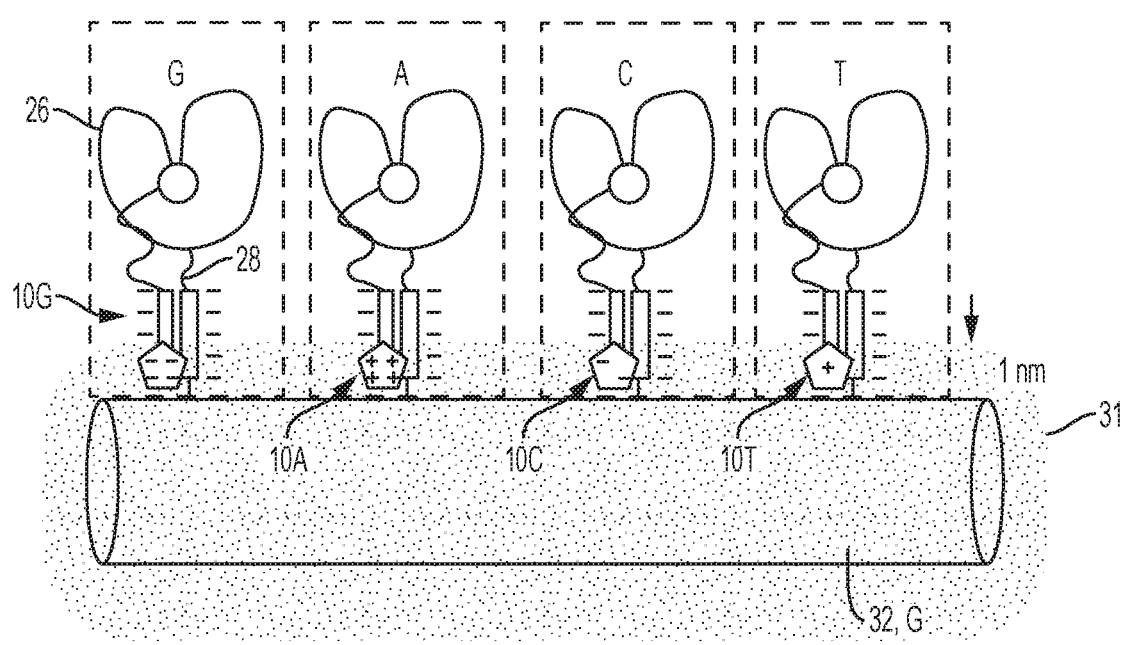
FIG. 3 is a schematic diagram of polymerases attached to an electrically conductive channel of a charge sensor and associated with labeled nucleotides that can be distinguished based on charge.

In one example, four different labeled nucleotides 10 are used in the fluid that is introduced to the charge sensor 35, each including a different nucleotide 12 (in particular a different base 20) and a different nucleotide-specific redox-active charge tag 18. An example of this is shown in FIG. 3. In this example, the labeled nucleotides 10 include: a first labeled nucleotide 10A including deoxyadenosine polyphosphate as the nucleotide and a first nucleotide-specific redox-active charge tag (shown with four positive charges in FIG. 3); a second labeled nucleotide 10G including deoxyguanosine polyphosphate as the nucleotide and a second nucleotide-specific redox-active charge tag (shown with four negative charges in FIG. 3); a third labeled nucleotide 10C including deoxycytidine polyphosphate as the nucleotide and a third nucleotide-specific redox-active charge tag (shown with two negative charges in FIG. 3); and a fourth labeled nucleotide 10T including deoxythymidine polyphosphate as the nucleotide and a fourth nucleotide-specific redox-active charge tag (shown with one positive charge in FIG. 3). In this example, the first, second, third, and fourth nucleotide-specific redox-active charge tags are different from each other.

In the example shown in FIG. 3, two of the first, second, third, and fourth nucleotide-specific redox-active charge tags are positively charged (e.g., dATP and dTTP) in the altered charge state (i.e., after the redox reaction takes place), and the other two of the first, second, third, and fourth nucleotide-specific redox-active charge tags (e.g., dGTP and dCTP) are negatively charged in the altered charge state (i.e., after the redox reaction takes place).

In the example shown in FIG. 3, even though the charges on two of the nucleotide-specific redox-active charge tags are the same (positive or negative), the tags 18 can still be used to distinguish the different types of nucleotides because the charges have different strengths (e.g., after redox activation). The example configuration shown in FIG. 3 provides four-state discrimination based on a single tether hybridization position and four different redox-active charge tags 18. Specifically, dGTP and dCTP both contain negatively charged redox-active charge tags 18 that distinguish them from dATP and dTTP; and dGTP can be distinguished from dCTP due to a charge that is distinguishably higher than the charge on dCTP. Similarly, dATP and dTTP can be distinguished from each other due to the higher positive charge on the dATP moiety compared to the dTTP moiety.

In some examples, it may not be feasible to have the redox-active charge-tags 18 of both positive and negative magnitudes operating in the same fluid, because the voltage required to charge a negative tag may discharge a positive tag, and vice versa. As such, in other examples, it may be desirable to utilize examples of the labeled nucleotides 10 disclosed herein that include redox-active charge-tags 18 of one polarity, and to use other labeled nucleotides that include permanently charged (i.e., not redox) tags. Examples of permanently charged tags include negatively charged tags such as, for example, a phosphate group, DMT and/or FMOC; or positively charged tags, such as a primary amine. As an example, from one to three different labeled nucleotides 10 (including the redox-active charge tags 18) may be used, and a remainder of the labeled nucleotides would include permanently charged tags and not redox-active charge tags 18. This is especially useful in the case where reducing or oxidizing conditions (but not both) are used. It is to be understood that agglomeration should not occur in these instances, because there is not a relatively high concentration of large moieties of both charge types in solution at the same time.

FIG. 3 also illustrates the sensing zone 31 (the shaded area around the gate G/electrically conductive channel 32). The charge sensors 35 may be operated at biologically relevant salt conditions, for example, in the about 1 mM to about 100 mM range. The Debye screening length of such salt solutions may be in a range of about 0.3 nm to about 10 nm, which may limit the sensing zone 31 to a few nm outside the surface of the gate G and often may reduce signal levels to the limit of detectability.

While several tethered polymerases 28 are shown on the electrically conductive channel 32 in FIG. 3, it is to be understood that in a particular charge sensor 35, one polymerase 28 is tethered to one electrically conductive channel 32. As such, the example shown in FIG. 3 illustrates the polymerase 28 during four different nucleotide incorporation events, and the effect on the different redox-active charge tags 18 during the respective incorporation events.

Figure 4:
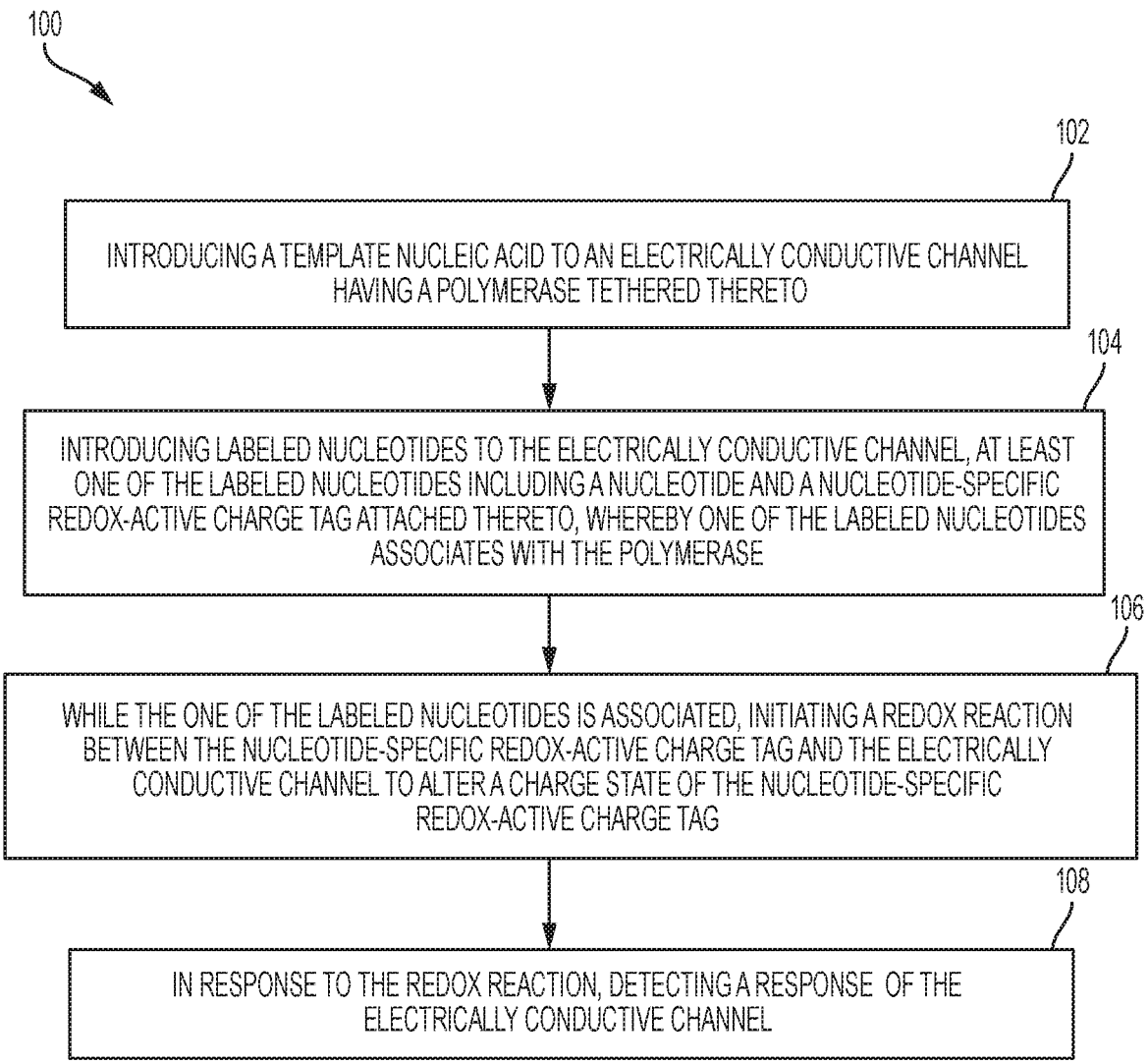
FIG. 4 is a flow diagram illustrating an example of a method disclosed herein.
Figure 5A:
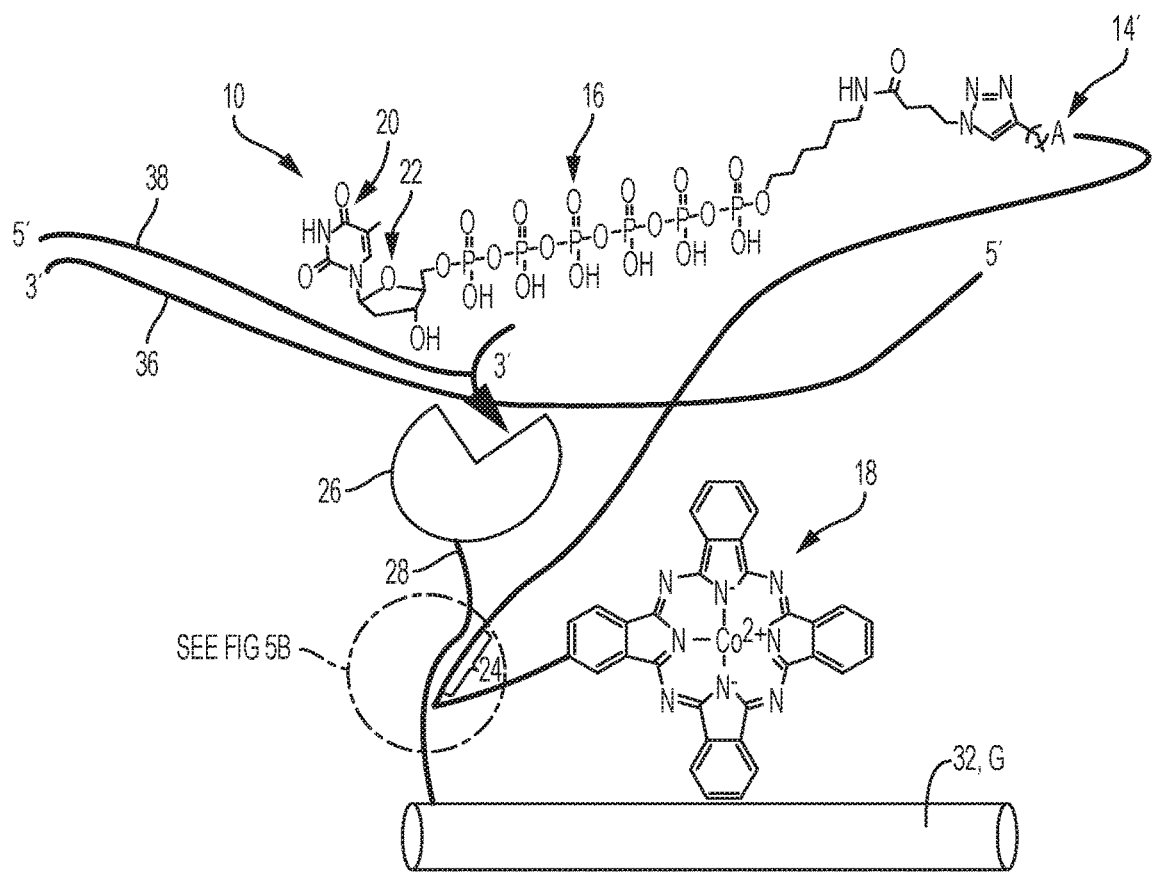
FIG. 5A is a schematic diagram of an example of a labeled nucleotide being used in a sequencing method.
Figure 5B:
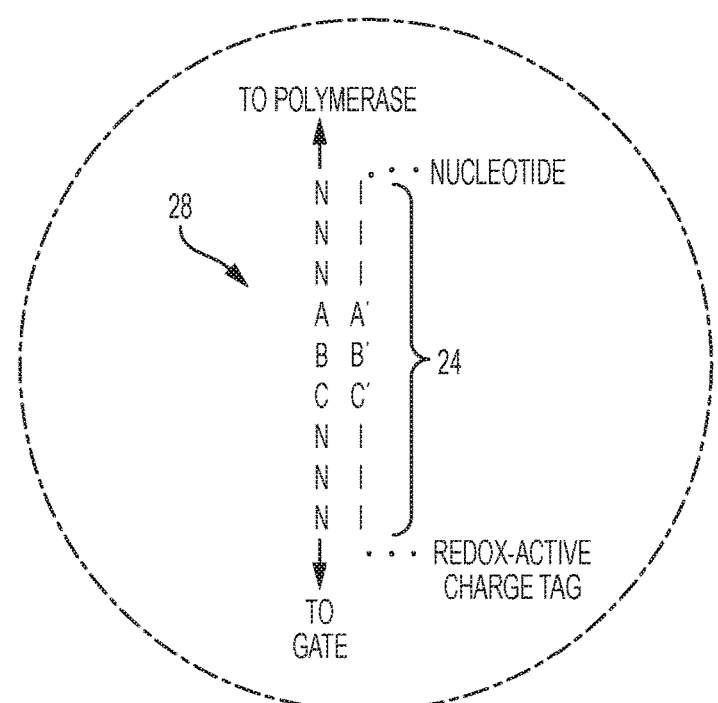
FIG. 5B is a schematic illustration of an example of the interaction between a tether and a specificity region of an example of the labeled nucleotide disclosed herein.

Referring now to FIG. 4, an example of a method is depicted. The method 100 include introducing a template nucleic acid 36 to an electrically conductive channel 32 having a polymerase 26 tethered thereto (reference numeral 102); introducing labeled nucleotides 10 to the electrically conductive channel 32, at least one of the labeled nucleotides 10 including a nucleotide 12 and a nucleotide-specific redox-active charge tag 18 attached thereto, whereby one of the labeled nucleotides 10 associates with the polymerase 26 (reference numeral 104); while the one of the labeled nucleotides 10 is associated, initiating a redox reaction between the nucleotide-specific redox-active charge tag 18 and the electrically conductive channel 32 to alter a charge state of the nucleotide-specific redox-active charge tag 18 (reference numeral 106); and in response to the redox reaction, detecting a response of the charge sensor 32 (reference numeral 108). FIGS. 5A and 5B will also be referenced throughout the discussion of the method 100.

As shown in FIG. 5A, the template nucleic acid 36 introduced to the charge sensor 32 may be held in place by the polymerase 26, which is tethered to the charge sensor 32. The template nucleic acid 36 shown in FIG. 5A may be a template strand of DNA.

Also as shown in FIG. 5A, the labeled nucleotide 10 may include a base 20 that is complementary to a target nucleic acid of the template nucleic acid 36. The labeled nucleotide 10 will be held in place, in part, by the polymerase 26 that is also bound to the template nucleic acid 36. If present, the specificity region 24 of the linking molecule 14' of the labeled nucleotide 10 may interact with the tether 28.

An example of the labeled nucleotide 10 associated with the tether 28 is shown in FIG. 5B. In this example, the linking molecule 14' of the labeled nucleotide 10 includes the specificity region 24 (e.g., A', B', C') which has an affinity for a portion (e.g., A, B, C) of the tether 28. In this particular example, the specificity region 24 (e.g., A', B', C') includes nucleotides or peptide nucleic acids that are complementary to nucleotides or peptide nucleic acids of the portion (e.g., A, B, C) of the tether 28. In another example, the specificity region 24 and the accepting region of the tether 28 may be non-nucleic acid moieties that have an affinity to each other. In still another example, the specificity region 24 may be a non-nucleic acid moiety that has an affinity for a hydrophobic polymer (one example of the tether 28). The specific binding between these regions can result from standard Watson-Crick base pairing. The specificity region 24, in this example, can also include inosines (I) flanking the A', B', C' nucleotide sequence. Inosines are universal bases, and thus can pair with all four native nucleotides of DNA. As such, additional binding interactions can result from interactions of the universal bases (e.g., inosine I) with native nucleotides on the tether 28. Thus, when the labeled nucleotide 10 is bound to polymerase 26 during incorporation, synergistic binding occurs between the specificity region 24 of the labeled nucleotide 10 and the tether 28, which greatly increases the stability of the interaction between the labeled nucleotide 10 and the tether 28.

When the linking molecule 14 of the labeled nucleotide 10 does not include the specificity region 24, it is to be understood that the labeled nucleotide 10 will be held in place by the interaction with the polymerase 26. The length of the linking molecule 14 can help to ensure that the redox-active charge tag 18 is held within the sensing zone 31 of the gate G/electrically conductive channel 32.

The interaction between the labeled nucleotide 10 and polymerase 26, or between the labeled nucleotide 10 and the polymerase 26 and the tether 28 causes the redox-active charge tag 18 to come within the sensing zone 31 of the electrically conductive channel 32. The interaction(s) also aids in maintaining the redox-active charge tag 18 within the sensing zone 31 for a time sufficient for efficient and complete charge transfer. The time may be up to tens of milliseconds. This relatively long interaction is unlike other labeled nucleotides 10 present in the solution, which may diffuse and briefly touch the electrically conductive channel 32. The brief interaction is not long enough for sufficient charge transfer to take place, and thus in these instances, the redox-active charge tag 18 is not charged and no response is detected by the charge sensor 32.

In the example shown in FIG. 5A, the copper phthalocyanine redox-active charge tag 18 of the labeled nucleotide enters a field (e.g., the sensing zone 31) that is within from about 1 nm to about 2 nm of the electrically conductive channel 32. Because the labeled nucleotide 10 is held in place, the redox-active charge tag 18 is in a position to be charged by the gate G/electrically conductive channel 32.

To initiate the redox reaction between the gate G/electrically conductive channel 32 (e.g., the silicon nanowire, carbon nanotube, etc.) and the redox-active charge tag 18, the voltage applied to the gate G/electrically conductive channel 32 may be adjusted to an oxidation voltage or a reduction voltage of the redox-active charge tag 18. When oxidized, the redox-active charge tag 18 loses electrons, and thus the gate G/electrically conductive channel 32 creates net positive charges to the redox-active charge tag 18. When reduced, the redox-active charge tag 18 gains electrons, and thus the gate G/electrically conductive channel 32 injects net negative charges to the redox-active charge tag 18. As a result of the redox reaction, the charge state of the redox-active charge tag 18 is altered. This altered highly charged state (e.g., compared to the state of the redox-active charge tag 18 prior to being charged, which is the non-oxidized or non-reduced state) perturbs the field around the electrically conductive channel 32 and produces a detectable signal.

The voltage applied to the electrically conductive channel 32 during the redox reaction and during detection may depend upon the redox-active charge tag 18 that is used. For example, the charging voltage may be different from the reading voltage, and thus the electrically conductive channel 32 may cycle between charging voltage(s) and reading voltage(s). In an example, initiating the redox reaction involves applying a charging voltage to the electrically conductive channel 32, and detecting the response of the electrically conductive channel 32 involves applying a reading voltage to the electrically conductive channel 32.

The response of the electrically conductive channel 32 after the redox reaction is indicative of the altered charge state of the redox-active charge tag 18. The response of the electrically conductive channel 32 after the redox reaction may also be indicative of the base 20 of the labeled nucleotide 10 because the redox-active charge tag 18 is nucleotide-specific (i.e., a specific tag 18 is selected for a specific base 20). As such, the method 100 may also involve associating the response of the electrically conductive channel 32 with the nucleotide-specific redox-active charge tag 18 of the associated one of the labeled nucleotides 10 (i.e., the labeled nucleotide 10 that has associated with the polymerase 26), and based on the nucleotide-specific redox-active charge tag 18, identifying the nucleotide (e.g., the base 20) of the associated labeled nucleotide 10 (i.e., the labeled nucleotide 10 that has associated with the polymerase 26).

The base 20 of the associated labeled nucleotide 10 will be incorporated into a nascent strand 38 that is hybridized to the template nucleic acid 36. This will, in turn, naturally break the bond between the phosphate group 16 of the labeled nucleotide 10 and the newly incorporated nucleotide base 20. For example, after incorporation of the nucleotide base 20 into the nascent strand 38, the bond between the alpha phosphate and the linking molecule 16 or between the alpha phosphate and beta phosphate is naturally cleaved. As a result, the remainder of the labeled nucleotide 10 (e.g., components 14 or 14' and 18) is free to dissociate from the nucleotide base 20 and diffuse away from the electrically conductive channel 32, thereby returning the field around the electrically conductive channel 32 to the state it was in before the association of the labeled nucleotide 10 with the polymerase 26. The appearance and disappearance of signal as the field around the electrically conductive channel 32 is perturbed and returned to the unperturbed state, respectively, can be correlated with incorporation of a nucleotide base 20 into the nascent strand 38 of the template nucleic acid 36. As such, examples of the method 100 also include cleaving (e.g., at the phosphate group 16) the nucleotide-specific redox-active charge tag 18 and the linking molecule 14, 14' from the associated one of the labeled nucleotides 10, whereby the nucleotide base 20 of the associated labeled nucleotide 10 is incorporated into a nascent strand 38 complementary to the template nucleic acid 36. Cleaving may involve waiting for the natural cleaving to occur. Since the signal returns to a baseline state between successive labeled nucleotide base 20 incorporations, the detection of homopolymeric segments within the nascent strand 38 along the template strand 36 is possible.

Some examples disclosed herein exploit synergistic binding of the labeled nucleotide 10 to the polymerase 26, alone or in combination with the tether 28, in order to bring and hold the redox-active charge tag 18 in proximity of the sensing zone 31 of the electrically conductive channel 32. The stability of the complex formed between the tether 28 and the specificity region 24 can be relatively low, such that the complex (between the specificity region 24 and the tether 28) does not form for labeled nucleotides 10 that are not also bound to the polymerase 26 (i.e., labeled nucleotides 10 that are free in solution do not substantially bind to the tether 28). In other words, the off rate of the complex can be sufficiently high that the lifetime is short. However, when a stable association is formed between the labeled nucleotide 10 and the polymerase 26, the local concentration of the linking molecule 14, 14' increases around the tether 28, thus resulting in a high on rate of the specificity region 24 to the tether 28. In this manner, the overall association time is greatly increased in the polymerase-associated state of a labeled nucleotide 10 compared to the non-associated state of free-floating labeled nucleotides 10. The synergistic effect of the affinities of the labeled nucleotide 10 for the polymerase 30, alone or in combination with the tether 28, allow substantial binding affinity overall. After natural cleaving by the polymerase 26 after nucleotide base 20 incorporation, the synergistic effect is lost and the charge tag 18 will also dissociate from the electrically conductive channel 32.

In the example method 100, the associating of the one of the labeled nucleotides 10 with the polymerase 28, the initiating of the redox reaction, the detecting, the associating of the response, and the identifying of the incorporated nucleotide base 20 together are a sequencing cycle. The method 100 may further include performing another sequencing cycle with another labeled nucleotide 10 that associates with the polymerase 26. Performing the next sequencing cycle may include allowing a next one of the labeled nucleotides 10 to associate with the polymerase 26; while the next one of the labeled nucleotides 10 is associated, initiating another redox reaction between another nucleotide-specific redox-active charge tag 18 and the charge sensor 32 to alter a charge state of the other nucleotide-specific redox-active charge tag 18; in response to the other redox reaction, detecting another response of the charge sensor 32; associating the other response of the charge sensor 32 with the other nucleotide-specific redox-active charge tag; and based on the other nucleotide-specific redox-active charge tag 18, identifying a nucleotide (base 20) of the next one of the labeled nucleotides 10 (i.e., that has associated with the polymerase 26). The other nucleotide-specific redox-active charge tag can be cleaved, and the nucleotide (base 20) of the next one of the labeled nucleotides 10 is incorporated into the nascent strand 38 complementary to the template nucleic acid 36. The sequencing cycle may be repeated.

In the examples disclosed herein, a waveform may also be utilized. The waveform may be monitored to determine when it reaches one or more threshold voltages for the redox potential of the redox-active charge tags 18 that have different redox potentials. In these instances, the change in the resulting current through the gate G/electrically conductive channel 32 may be used as information to identify the base 20 of the labeled nucleotide 10 including the redox-active charge tag 18 that is associated with the particular threshold voltage.

In the examples disclosed herein, the number of electrons transferred to or from the redox-active charge tag 18 may also be monitored. The transferred number of electrons may be used to identify the nucleotide base 20 associated with the polymerase 26, and that the polymerase 26 incorporates into the nascent strand 38.

The labeled nucleotides 10 and system 10 disclosed herein may be used for any of a variety of applications. As described in reference to FIGS. 4, 5A and 5B, a particularly useful application is nucleic acid sequencing, such as single molecule sequencing-by-synthesis (SBS). In single molecule SBS, extension of a nucleic acid primer along a template nucleic acid 36 (e.g., a target nucleic acid or amplicon thereof) is monitored to determine the sequence of nucleotides in the template 36. The underlying chemical process can be polymerization (e.g., as catalyzed by a polymerase enzyme 26 as described herein). In a particular polymerase-based single molecule SBS example, nucleotides (e.g., bases 20) are added to a primer (thereby extending the primer and forming a nascent strand 38) in a template dependent fashion such that detection of the order and type of nucleotides added to the primer can be used to determine the sequence of the template. A plurality of different templates 36 at different electrically conductive channels 32 of an array can be subjected to the single molecule SBS technique under conditions where events occurring for different templates 36 can be distinguished by individual detectors that are operatively connected to each of the electrically conductive channels 32. Each electrically conductive channel 32 (and its source and drain terminals S, D) may be positioned within a depression or well of the flow cell, which helps to physically isolate one channel 32 from an adjacent channel 32 in an array.

Other suitable applications for the labeled nucleotides 10, kit, and system 30 disclosed herein include sequencing-by-ligation and sequencing-by-hybridization. Another useful application for the labeled nucleotides 10 and system 30 disclosed herein is gene expression analysis. Gene expression can be detected or quantified using RNA sequencing techniques, such as those referred to as digital RNA sequencing. RNA sequencing techniques can be carried out using sequencing methodologies known in the art such as those set forth above except that fluorescence detection of optically labeled nucleotides can be replaced with the charge-based detection methods set forth herein. Gene expression can also be detected or quantified using hybridization techniques carried out by direct hybridization to an array or using a multiplex assay, the products of which are detected on an array. These methods can be readily adapted by replacing optical labels and fluorescence detection with the charge-based detection techniques, and redox-active charge tags 18 set forth herein.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

The terms "substantially" and "about" used throughout this disclosure, including the claims, are used to describe and account for small fluctuations, such as due to variations in processing. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

Furthermore, it is to be understood that the ranges provided herein include the stated range and any value or sub-range within the stated range, as if such value or sub-range were explicitly recited. For example, a range represented by from about 1 charge to about 100 charges, should be interpreted to include not only the explicitly recited limits of from about 1 charge to about 100 charges, but also to include individual values, such as about 5 charges, 50 charges, 75 charges, etc., and sub-ranges, such as from about 15 charges to about 85 charges, etc.

While several examples have been described in detail, it is to be understood that the disclosed examples may be modified. Therefore, the foregoing description is to be considered non-limiting.

What is claimed is:

1. A labeled nucleotide, comprising:
   a nucleotide;
   a linking molecule attached to a phosphate group of the nucleotide; and
   a redox-active charge tag attached to the linking molecule, wherein the redox-active charge tag is selected from the group consisting of zinc tetrabenzoporphyrin, cobalt phthalocyanine, tris-(2,2'-bipyrimidine)ruthenium, 4-ferrocenylbenzyl alcohol, 5-(4-hydroxymethylphenyl)-10,15,20-trimesitylporphinatozinc(II), and a redox-active calixarene, and wherein the redox-active charge tag is to be oxidized or reduced by an electrically conductive channel when maintained in proximity of a sensing zone of the electrically conductive channel.

2. The labeled nucleotide as defined in claim 1, wherein the linking molecule comprises a specificity region attached to the redox-active charge tag.

3. The labeled nucleotide as defined in claim 2, wherein the specificity region is to interact with an acceptor region on a tether bound to the electrically conductive channel, and the specificity region includes an affinity tag.

4. The labeled nucleotide as defined in claim 3, wherein the specificity region is to hybridize to the acceptor region on the tether bound to the electrically conductive channel, and the affinity tag includes a nucleotide sequence including from about one nucleotide to about ten nucleotides or a peptide nucleic acid sequence including from about one peptide nucleic acid to about ten peptide nucleic acids.

5. The labeled nucleotide as defined in claim 1, wherein:
   the redox-active charge tag includes 10 charges or fewer in a non-oxidized or non-reduced state; and
   the redox-active charge tag includes from about 1 charge to about 100 charges in an oxidized or reduced state.

6. A method, comprising:
   introducing a template nucleic acid to an electrically conductive channel having a polymerase tethered thereto;
   introducing labeled nucleotides to the electrically conductive channel, at least one of the labeled nucleotides including a nucleotide and a nucleotide-specific redox-active charge tag attached thereto, whereby one of the labeled nucleotides associates with the polymerase;
   while the one of the labeled nucleotides is associated, applying a charging voltage to the electrically conductive channel, thereby initiating a redox reaction between the nucleotide-specific redox-active charge tag and the electrically conductive channel to alter a charge state of the nucleotide-specific redox-active charge tag; and
   in response to the redox reaction, applying a reading voltage to the electrically conductive channel, thereby detecting a response of the electrically conductive channel.

7. The method as defined in claim 6, further comprising:
associating the response of the electrically conductive channel with the nucleotide-specific redox-active charge tag of the associated one of the labeled nucleotides; and
based on the nucleotide-specific redox-active charge tag, identifying the nucleotide of the associated labeled nucleotide.

8. The method as defined in claim 7, further comprising cleaving the nucleotide-specific redox-active charge tag from the associated one of the labeled nucleotides, whereby the nucleotide of the associated labeled nucleotide is incorporated into a nascent strand complementary to the template nucleic acid.

9. The method as defined in claim 8, wherein:
the associating of the one of the labeled nucleotides, the initiating of the redox reaction, the detecting, the associating, and the identifying together are a sequencing cycle; and
the method further comprises:
performing a next sequencing cycle by:
allowing a next one of the labeled nucleotides to associate with the polymerase;
while the next one of the labeled nucleotides is associated, initiating an other redox reaction between an other nucleotide-specific redox-active charge tag and the electrically conductive channel to alter a charge state of the other nucleotide-specific redox-active charge tag;
in response to the other redox reaction, detecting an other response of the electrically conductive channel;
associating the other response of the electrically conductive channel with the other nucleotide-specific redox-active charge tag; and
based on the other nucleotide-specific redox-active charge tag, identifying the nucleotide of the next one of the labeled nucleotides.

10. The method as defined in claim 9, further comprising:
cleaving the other nucleotide-specific redox-active charge tag, whereby the nucleotide of the next one of the labeled nucleotides is incorporated into the nascent strand complementary to the template nucleic acid; and
repeating the sequencing cycle.

11. The method as defined in claim 6, wherein the redox-active charge tag is selected from the group consisting of zinc tetrabenzoporphyrin, cobalt phthalocyanine, tris-(2, 2'-bipyrimidine)ruthenium, 4-ferrocenylbenzyl alcohol, 5-(4-hydroxymethylphenyl)-10,15,20-trimesitylporphinatozinc(II), and a redox-active calixarene.

12. The method as defined in claim 6, wherein:
the redox-active charge tag includes 10 charges or fewer in a non-oxidized or non-reduced state; and
the redox-active charge tag includes from about 1 charge to about 100 charges in an altered charge state.

13. The method as defined in claim 6, wherein:
the labeled nucleotides include:
a first labeled nucleotide including deoxyadenosine polyphosphate as the nucleotide and a first nucleotide-specific redox-active charge tag;
a second labeled nucleotide including deoxyguanosine polyphosphate as the nucleotide and a second nucleotide-specific redox-active charge tag;
a third labeled nucleotide including deoxycytidine polyphosphate as the nucleotide and a third nucleotide-specific redox-active charge tag; and
a fourth labeled nucleotide including deoxythymidine polyphosphate as the nucleotide and a fourth nucleotide-specific redox-active charge tag; and
the first, second, third, and fourth nucleotide-specific redox-active charge tags are different from each other.

14. The method as defined in claim 13, wherein two of the first, second, third, and fourth nucleotide-specific redox-active charge tags are positively charged in an altered charge state, and wherein an other two of the first, second, third, and fourth nucleotide-specific redox-active charge tags are negatively charged in the altered charge state.

15. The method as defined in claim 6, wherein the labeled nucleotides are present in a low salt buffer.

16. The method as defined in claim 6, wherein the electrically conductive channel is a channel of a field effect transistor.

17. A kit, comprising:
a flow cell, including:
an electrically conductive channel having a tether attached thereto; and
a polymerase attached to the electrically conductive channel via the tether;
a template nucleic acid to be introduced into the flow cell;
reagents to be introduced into the flow cell, the reagents including labeled nucleotides, at least one of the labeled nucleotides including:
a nucleotide;
a linking molecule attached to a phosphate group of the nucleotide; and
a redox-active charge tag attached to the linking molecule, wherein the redox-active charge tag is selected from the group consisting of zinc tetrabenzoporphyrin, cobalt phthalocyanine, tris-(2,2'-bipyrimidine) ruthenium, 4-ferrocenylbenzyl alcohol, 5-(4-hydroxymethylphenyl)-10,15,20-trimesitylporphinatozinc(II), and a redox-active calixarene, and wherein the redox-active charge tag is to be oxidized or reduced by the electrically conductive channel when maintained in proximity of a sensing zone of the electrically conductive channel; and
a detector to detect a response from the electrically conductive channel when a redox reaction takes place between the redox-active charge tag and the electrically conductive channel.

18. The kit as defined in claim 17, wherein:
the redox-active charge tag includes 10 charges or fewer in a non-oxidized or non-reduced state; and
the redox-active charge tag includes from about 1 charge to about 100 charges in an oxidized or reduced state.

19. The kit as defined in claim 17, wherein the electrically conductive channel is a channel of a field effect transistor.

20. The labeled nucleotide as defined in claim 1, wherein the linking molecule includes:
an alkyl chain, an amide group, a poly(ethylene glycol) chain, and a triazole; or
alkyl chains, an amide group, poly(ethylene glycol) chains, a triazole, and a phosphate group; or
alkyl chains, amide groups, poly(ethylene glycol) chains, a triazole, and a phosphate group.

* * * * *